(12) United States Patent
Biebernik et al.

(10) Patent No.: US 6,432,363 B2
(45) Date of Patent: Aug. 13, 2002

(54) OPTOCHEMICAL SENSOR

(75) Inventors: Karin Biebernik, Turramurra (AU); Franz Reininger, St. Nikolai i.S.; Wolfgang Trettnak, Mooskirchen, both of (AT)

(73) Assignee: Joanneum Research Forschungagesellschaft mbH, Graz (AT)

( * ) Notice: Subject to any disclaimer, the term of this patent is extended or adjusted under 35 U.S.C. 154(b) by 0 days.

(21) Appl. No.: 09/802,971

(22) Filed: Mar. 12, 2001

Related U.S. Application Data

(63) Continuation of application No. PCT/AT99/00225, filed on Sep. 15, 1999.

(30) Foreign Application Priority Data

Sep. 15, 1998 (AT) .............................................. 1550/98

(51) Int. Cl.⁷ .............................................. G01N 21/64
(52) U.S. Cl. .................................. 422/82.07; 422/82.08
(58) Field of Search ........................... 422/82.05, 82.07, 422/82.08, 82.11; 250/458.1, 459.1

(56) References Cited

U.S. PATENT DOCUMENTS

| | | | | |
|---|---|---|---|---|
| 4,827,121 A | * | 5/1989 | Vidrine et al. | 250/227.23 |
| 4,925,268 A | * | 5/1990 | Iyer et al. | 385/12 |
| 4,945,245 A | * | 7/1990 | Levin | 250/458.1 |
| 5,028,395 A | | 7/1991 | Sebille et al. | 422/82.06 |
| 5,298,327 A | * | 3/1994 | Zarian et al. | 264/1.24 |
| 5,640,470 A | | 6/1997 | Iyer et al. | 385/12 |
| 5,837,804 A | * | 11/1998 | Yamagishi et al. | 264/331.19 |
| 5,965,642 A | * | 10/1999 | Gouterman et al. | 524/88 |
| 6,074,607 A | * | 6/2000 | Slovacek et al. | 422/82.05 |
| 6,143,570 A | * | 11/2000 | Alder et al. | 422/57 |
| 6,190,612 B1 | * | 2/2001 | Berger et al. | 422/82.07 |
| 6,237,397 B1 | * | 5/2001 | Shinar et al. | 310/313 R |
| 6,252,024 B1 | * | 6/2001 | Barnard et al. | 526/259 |

FOREIGN PATENT DOCUMENTS

| | | |
|---|---|---|
| DE | 3148830 A1 | 6/1983 |
| DE | 3346810 A1 | 7/1984 |
| EP | 0190829 A2 | 8/1986 |
| EP | 0550424 A2 | 7/1993 |
| EP | 0601816 A2 | 6/1994 |
| EP | 0824212 A1 | 2/1998 |
| WO | WO87/00023 | 1/1987 |
| WO | WO97/11067 | 3/1997 |

OTHER PUBLICATIONS

J. S. Sirkis et al, Journal of Lightwave Technology, No. 8, "Analysis of a Damage Sensor . . . ", pp. 1385–1393, Aug. 11, 1993.

* cited by examiner

*Primary Examiner*—Jeffrey Snay
(74) *Attorney, Agent, or Firm*—Jacobson Holman, PLLC

(57) ABSTRACT

The invention relates to an optochemical sensor consisting of a polymer matrix and a luminescent colorant material contained therein, whose emission power may be modified by the substances to be detected after being excited with electro-magnetic radiation. The polymer matrix is formed by at least one polymer, wherein no plasticizers have been added, which polymer contains phenyl groups in the main chain and may also be sterilized. the invention also relates to a method for producing the disclosed optochemical sensor, wherein a solution of a polymer is prepared, wherein 0.01 to 100 mMol luminescent colorant material per polymer is added to the solution and the mixture is solidified to obtain a homogenous membrane.

13 Claims, 1 Drawing Sheet

Pt Octaethylporphyrinketone in PSU

US 6,432,363 B2

OPTOCHEMICAL SENSOR

The present application is a continuation application of PCT/AT99/00225, filed on Sep. 15, 1999.

BACKGROUND OF THE INVENTION

1. Field of the Invention

The present invention relates to an optochemical sensor comprised of a polymer matrix and a luminescent dye incorporated therein, whose emission capacity is variable upon excitation with an electromagnetic radiation, in particular light, by detectable substances such as gaseous or dissolved $O_2$, $SO_2$, $H_2O_2$, $Cl_2$, nitrogen oxides, halogenated hydrocarbons, wherein the polymer matrix is formed of at least one polymer without addition of plasticizers, which polymer contains phenyl groups in its main chain, as well as a method for producing an optochemical sensor whose emission capacity is variable upon excitation with an electromagnetic radiation, in particular light, by detectable substances such as gaseous or dissolved $O_2$, $SO_2$, $H_2O_2$, wherein an at least 1 to 25 wt.-% solution of a polymer containing phenyl groups in its main chain is prepared in an organic solvent and the mixture is cured to form a homogenous membrane.

2. Description of the Prior Art

Sensors for measuring the concentration of defined substances or gases in solutions or solids, for instance in biological material, usually operate electromechanically and involve the drawback that, in quantitatively detecting the gas to be determined, they will consume a portion of the substance to be determined, thus falsifying the measuring result. In order to exclude during a measuring procedure, any change of the concentration of the substance to be measured, optochemical sensors have recently been developed, which are characterized in that they do not modify the composition of the analyte, but indicate the quantitative detection of the concentration of the substance to be detected merely by extinguishing the luminescence of the luminescent substance incorporated in the sensor with characteristic parameters such as, for instance, the luminescence intensity, the phase shift of the luminescence signal or the decay period of the luminescence being examined. The quantitative detection of the substances to be measured is feasible by comparing the luminescence signal with a calibration function, for instance, by means of an electronic data processor.

A sensor, as well as a method for producing the same, of the initially defined kind may be taken, for instance, from EP-A 0 550 424, which mentions specific polymers in which gases such as, for instance, oxygen and $CO_2$ are to be readily dissolvable. Other optochemical sensors of similar types are disclosed, for instance, in WO 97/11067 and EP-A 0 601 816, wherein, due to the polymers used, none of those sensors allows sterilization, in particular by applying elevated temperatures, and hence subsequent usability in biological materials.

From DE-A 33 46 810, a method and a device for determining the concentration of oxygen in a gaseous or liquid environment have become known, which are based on luminescence quenching, using the shortened service life or reduced emission intensity of certain metal complexes in the presence of oxygen for determining the content of oxygen.

Furthermore, a device for determining the concentration of oxygen in gases, liquids and tissues has become known, for instance, from DE-A 31 48 830, in which the gas concentration of the measuring sample is determined by irradiating a luminescent surface formed by a "single-grain" layer applied on a transparent substrate by means of a bonding or adhesive layer, with light of a defined wavelength, exposing said surface to the measuring sample and measuring the reduction of the light emission of said surface. However, that known device, which may be readily employed for defined measuring ranges of the oxygen content contained in the measuring probe, involves the drawback that the optochemical sensor employed cannot be purified or sterilized by chemical methods either before or after having carried out a measurement, and hence, in principle, is hardly usable in biological material and if so, to a limited extent only.

An optical sensor for monitoring the partial pressure of oxygen which operates in a manner substantially analogous to that of DE-A 31 48 830 is known also from EP-A 0 190 829, wherein, however, the optochemical sensor employed in that device is embedded in a polymer matrix containing a plasticizer such that the sensor may be used only in conjunction with substances, solutions or materials that will not dissolve out of the sensor the plasticizer incorporated in the matrix.

From WO 87/00023 are known methods for measuring the concentration of oxygen by the aid of optochemical sensors, wherein also the sensors used in those methods have the disadvantage of frequently containing plasticizers or being made of materials unable to resist thermal treatment and/or chemical treatment, so that the sensor cannot be subjected to purification and sterilization either before or after its use.

SUMMARY OF THE INVENTION

The present invention, thus, aims to provide an optochemical sensor which may be repeatedly purified and/or sterilized and, thus, may be exposed to elevated temperatures so as to be applicable for the measurement of substances to be detected, in particular in the gaseous state or in gases present in the dissolved state, in biological materials and, in particular fermenter solutions.

To solve these objects, the optochemical sensor according to the invention, departing from a sensor of the initially defined kind, is essentially characterized in that the polymer is selected from polysulfones, polyether sulfones, polyether imides and/or polyoxyphenylenes and that the polymer has a glass transition temperature of above 140° C. Since the polymer or carrier matrix is comprised of at least one pure polymer containing phenyl groups in its main chain, wherein it is provided according to the invention that the polymer is selected from polysulfones, polyether sulfones, polyether imides and/or polyoxyphenylenes, a matrix for the optochemical sensor is formed, which matrix will be sufficiently stable to be subjected to a sterilization and/or chemical purification treatment without changing its composition, mechanical, thermal and optical stabilities or any other physicochemical properties. Such a stability relative to both physicochemical purification procedures and sterilization, e.g., by means of elevated temperatures and pressures is important, in particular, in the application of the optochemical sensor according to the invention for measuring the oxygen content in biological material, and enables the sensor to be arranged, for instance, directly in a fermenter during the fermentation process, supplying continuously reproducible values during the entire period of the fermentation process without involving the risk that substances will be dissolved out of the sensor material or migrate into the fermentation broth, which cause impurities of the fermenter content and subsequently can be eliminated from the fermenter content not at all or only with great difficulties, thus constituting permanent possibly deleterious impurities, for instance, in food and semiluxuries.

The matrices proposed according to the invention, which are made of polysulfones, polyether sulfones, polyether imides and/or polyoxyphenylenes, after manufacturing and curing are sufficiently flexible to form sensor films in which luminescent dyes may be present in the dissolved state or in a homogenously distributed manner and, at the same time, are sufficiently stable to resist chemicals like those contained in solutions of biological materials or directly in biological materials and even those used for the purification and regeneration of the sensor. The polymers, furthermore, may be selectively dissolved in specific organic solvents, for instance, in order to reach a uniform distribution of the luminescence dye or luminescent colorant material within the matrix of the sensor. Moreover, a matrix formed of such a polymer is highly permeable to light, hardly exhibits any intrinsic luminescence and is sufficiently photostable, too. In addition, biocompatibility tests with sensors of the invention, in particular those containing polysulfone sensor membranes, revealed that no toxic influence was to be detected on materials getting into contact with said membranes.

In order to enable the repeated sterilization and purification of the optochemical sensor, it is, furthermore, provided according to the invention that the polymer has a glass transition temperature of above 140° C. Due to the fact that the polymer used as a matrix has a glass transition temperature of above 140° C., it is ensured that no softening of the matrix and hence possibly nonuniform distribution of the luminescent dye caused, in particular, by migration or aggregation of the dye molecules, will occur during sterilization even if elevated temperatures are exerted on the sensor.

In order to obtain reproducible values for the substance(s) to be detected, in particular the substances $O_2$, $SO_2$, $H_2O_2$, $Cl_2$, nitrogen oxides, halogenated hydrocarbons, over largely any concentration ranges of the same, the optochemical sensor according to the invention preferably is developed further such that the amount of luminescent dye incorporated in the polymer is 0.01 to 100 mMol dye per kg polymer, in particular 0.1 to 20 mMol dye per kg polymer. Even if only slight amounts of dye are used, it will, therefore, be feasible to provide a sensor which is applicable for obtaining reproducible measurements of substances to be detected, in particular gaseous or dissolved oxygen. In addition, the optochemical sensor according to the invention stands out for its low manufacturing costs, since only small amounts of expensive luminescent dyes are incorporated therein.

In a particularly preferred manner and, in particular, in order to obtain a sterilizable sensor in which the dye remains uniformly distributed, the luminescent dye incorporated in the matrix is chosen such that the luminescent dye incorporated in the polymer matrix is a dye that is stable up to at least 150° C. and selected from the group consisting of the inorganic salts of transition metal complexes having α-diimine ligands, such as, tris(4,7-diphenyl-1,10-phenanthroline) ruthenium(II) salts, tris(1,10-phenanthroline) ruthenium(II) salts and tris-2,2'-bipyridyl ruthenium(II) salts; or of terpyridine, such as osmium terpyridine; the transition metal complexes of porphyrines or porphyrine derivatives, such as complexes of the tetraphenylporphyrine of Pt or Pd, of the octaethylporphyrine ketone of Pt or Pd, of the tetrapentafluorophenylporphyrine of Pt or Pd, or of the octaethylporphyrine of Pt or Pd; of polycyclic aromatic hydrocarbons such as decacyclene, pyrene or its derivatives, or campherchinone. The dyes incorporated in the optochemical sensor according to the invention, dissolved in the above-mentioned polymers, both are sterilizable, i.e., not modifiable or decomposable, by heat, pressure and even chemical substances such as diluted acids and bases used for chemical purification, and, in addition, stand out for their capability to yield reproducible measuring results at the most different concentrations of the substance to be measured and/or determined. On account of its versatility, for instance, on account of its compatibility with fiber optics, such a sensor may, furthermore, be used also for measurements to be carried out on inaccessible sites such as boreholes.

In order to be able to provide, in particular, a sensor that is stable against mechanical deformation, the sensor according to the invention preferably is further developed such that the optochemical sensor is applied on a substrate. In order to avoid falsified measuring results caused by the substrate material, the substrate used for the optochemical sensor according to the invention preferably is further developed such that optically inactive light-permeable polymers that are insoluble, or resistant, in organic solvents, acids, bases and water, such as, for instance, polyesters like PET, polymethylmethacrylate or glass, are used. Such materials which are suitable as substrates are characterized in that they exhibit a negligible intrinsic luminescence, neither emit or absorb in the range in which the luminescent dye emits or absorbs, nor are soluble or vulnerable in solvents in which, for instance, the matrix is soluble. A stable substrate may thus be made available, on which the chemically sensitive layer can be fixed or applied in order to obtain an increased mechanical stability of the overall system. A sensor made of such materials is stable also against elevated pressures and may be used, for instance, even for applications in the deep sea.

Finally, the optochemical sensor in accordance with a preferred advancement of the present invention may be covered by an optically insulating layer permeable to the substance to be analyzed. Such an insulation layer is beneficial, in particular, if luminescent substances are contained, or supposed to be contained, in the medium to be analyzed, for instance, in order to thereby create an optical screen, a screen against ambient light or a screen against environmental impacts on the sensor. In accordance with a preferred further development of the invention, the optically insulating layer may, moreover, be comprised of coarsely porous polytetrafluoroethylene, copolymers consisting of 2,2-bis-trifluoromethyl-4,5-difluoro-1,3-dioxolene and tetrafluoroethylene, or silicone, such an optically insulating layer, thus, not only rendering feasible the above-mentioned advantages of a screen, but also ensuring a mechanical and additional chemical protection of the sensor surface while, at the same time, safe-guarding the penetration of the substance to be analyzed to the sensor surface. Among the copolymers consisting of 2,2-bis-trifluoromethyl-4,5-difluoro-1,3-dioxolene and tetrafluoroethylen, that marketed under the name Teflon AF (Teflon AF being a trademark of E.I. Du Pont de Nemours and Company) has proved to be particularly suitable.

Furthermore, the present invention aims to provide a method for producing a sterilizable, in particular, repeatedly sterilizable optochemical sensor hence capable of being exposed to elevated temperatures, which may be used for the detection of substances like $O_2$, $SO_2$, $H_2O_2$, $Cl_2$, nitrogen oxides, halogenated hydrocarbons and, in particular, gases like $SO_2$ contained in biological materials. Departing from the method of the initially defined kind, the method according to the invention is essentially characterized in that 0.01 to 100 mMol luminescent dye per kg polymer is added to the solution and the optochemical sensor is subsequently dried in a furnace at 100 to 150° C. for 30 minutes to 24 hours for its completion. By preparing, according to the invention, a solution of a polymer, a luminescent dye and a solvent to be evaporated, it is feasible to provide an optochemical sensor in which the slight amounts of luminescent dye incorporated therein are uniformly distributed over the total volume of the sensor, whereby reproducible measuring values will be obtained by means of the sensor at any point of the sensor, the uniform distribution of the luminescent dye particles remaining unchanged or unaffected even after repeated sterilization procedures. The choice of the relative molar mass of the polymer used is not critical. The lower limit is determined by that molar mass at which the polymer is able to form a solid layer and no longer is to be regarded as a viscous liquid. The upper limit is determined by the solubility characteristics of the polymer. In order to ensure the complete elimination of the organic solvents used for the production of the sensor, the sensor, according to the invention, additionally is subsequently heated in a furnace at 100° C. to 150° C. for 30 minutes to 24 hours for its completion so as to reliably ensure the elimination of any traces of the solvents used for the preparation of the solution of polymer matrix and luminescent dye.

In order to have the matrix polymer selectively dissolved in the method according to the invention of producing the sensor, the method according to the invention preferably is advanced in a manner that organic solvents such as toluene, chloroform and/or methylene chloride or a mixture thereof are used. The solvents used according to the invention, in particular, are chosen such that they will be quantitatively removed from the sensor membrane in a drying procedure optionally following the manufacturing process, so that, in case the sensor is used in biological materials such as, for instance, fermenter solutions, there will be no risk of the assay or test substances being contaminated by solvents diffusing into the material.

In the production of a sensor it may, for instance, be proceeded according to various known methods such as spin coating; application of the sensor layer and/or the optically insulating layer on a substrate by means of a doctor blade; printing of the sensor layer on a substrate or, if the optically insulating layer is to be impressed, on the sensor membrane; an example of this being tampon printing. The optical insulation, too, may serve as a substrate if the application of the sensitive layer is effected on an analyte-permeable layer simultaneously serving as an optical insulation.

In order to enable the optochemical sensor according to the invention to be used, in particular, for analyzing biological materials and immersed, for instance, directly into fermenter solutions without contaminating the substances to be fermented, the method according to the invention for producing a sensor is advanced such that the sensor is sterilized at a temperature of between 100° C. and 150° C. and a pressure of between 1.2 bar and 4 bars for 20 to 90 minutes. By selectively choosing the polymers used for the production of the sensor, and the respective luminescent dyes, it has become feasible to sterilize the sensor at elevated temperatures and pressures for extended periods of time, said sterilizing procedure being repeatable several times without affecting the properties or measuring accuracy of the sensor. The option to sterilize the sensor and even dry it in a furnace, renders the sensor applicable in all fields where it is essential that the substances to be assayed will not be contaminated by molecules dissolved out, or diffusing out, of the sensor and which call for high measuring accuracies even at elevated temperatures of the sensors.

According to the invention, the sterilization of the sensor is carried out using hot vapor, $H_2O_2$, ethanol or $\beta$- or $\gamma$-rays, wherein sterilization with hot vapor at elevated pressures is particularly preferred and, according to the invention, is feasible, for instance, in that the polymer material employed in the production of the sensor has an elevated glass transition temperature, thus safely avoiding any modification of the sensor material in the course of the sterilization procedure, in particular, a flow of the sensor material and hence a nonuniform distribution of the luminescent dye caused, for instance, by the crystallization of the dye.

In order to enable the sensor according to the invention to be used repeatedly in different applications, the method according to the invention is further developed such that the sensor is purified by immersion into an about 1 N acid or lye, in particular, phosphoric acid, NaOH, KOH, for 10 to 40 minutes at temperatures of between 20 and 90° C. Such a purification procedure of the optochemical sensor according to the invention may be realized before or after sterilization so as to safely eliminate also impurities deposited on the surface of the sensor.

Description of the preferred embodiments of the invention

In the following, the invention will be explained in more detail by way of exemplary embodiments which illustrate the production of sensors incorporating membranes prepared of various organic polymers containing a phenyl group, with reference to the annexed drawings.

EXAMPLE 1

Production, calibration and sterilization of an optochemical sensor 0.31 g polysulfone by Aldrich are mixed with 2,81 g chloroform and the polymer is dissolved in the solvent by agitation at room temperature. 1.25 g of the polymer solution are removed and stirred with 0.0017 g tris(4,7-diphenyl-1,10-phenanthroline ruthenium(II) perchlorate at room temperature. The solution is applied on 175 $\mu$m substrate layers, in particular a polyester film, by means of a doctor blade as a thin coat having a thickness of 50 $\mu$m. After drying for a maximum of one hour at room temperature, the thus produced films are left in the drying closet at about 138° C. for approximately 16 hours.

For the purpose of calibration, the phase shift of the luminescent membrane was measured as a function of the oxygen partial pressure. After this, the membrane was treated in an autoclave at about 134° C. for 60 minutes at approximately 2 bars, allowed to dry for about 15 hours at room temperature in the dark and subjected to another phase shift determination. The procedure of the treatment in the autoclave, drying and measuring was carried out four times.

Figure 1:
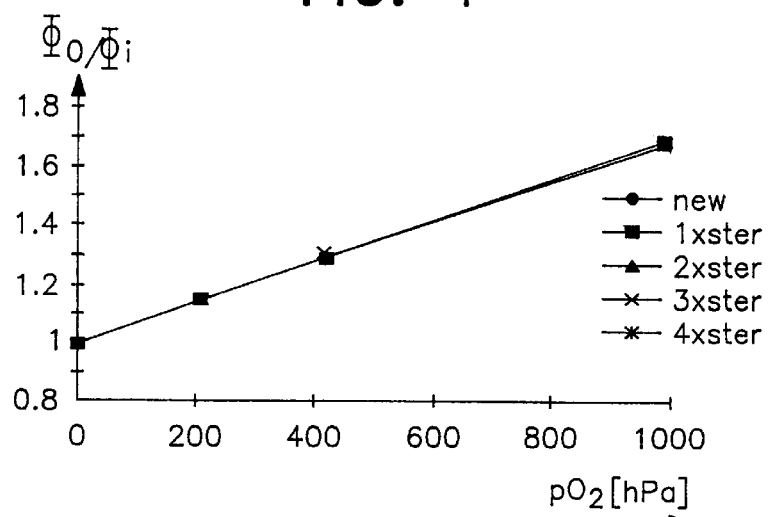
FIGS. 1–3 depict calibration functions of optochemical sensor membranes according to the invention.

FIG. 1 depicts the calibration function with oxygen-containing calibration gases, of a new membrane and of membranes treated in the autoclave once, twice, three times and four times, respectively, wherein the partial pressure of oxygen is plotted on the abscissa and the standardized phase shift of the luminescent membrane is plotted on the ordinate. From this illustration, the constancy of the slope $K_{sv}$ of the Stern Volmer plots of the indicator membranes is apparent.

If the polysulfone membrane is dried at about 135° C. and subsequently treated in the autoclave at approximately 134° C., the deviation of the membrane treated four times in the autoclave from the calibration function of the same membrane after its first sterilization corresponds to the values indicated in the Table below. The first sterilization in this context is to be regarded as a pretreatment of the sensor.

| Vol.-% $O_2$ content in calibration gas | (Drying at about 135° C.); comparison of membranes sterilized 4 and 1 times |
|---|---|
| 0 | 0.11 |
| 5.1 | −0.03 |
| 10.3 | −0.18 |
| 20.55 | −0.48 |
| 41.96 | −0.99 |
| 100 | −1.93 |

EXAMPLE 2

Production, calibration and sterilization of an optochemical sensor 0.10 g polyether imide "Ultem 1000" by General Electric are mixed with 1.15 g chloroform and the polymer is dissolved under agitation at room temperature. The polymer solution is mixed with 0.001 g tris(4,7-diphenyl-1,10-phenanthroline) ruthenium(II) perchlorate and agitated. By doctoring, layers having wet film thicknesses of 50 μm are applied on a Mylar polyester membrane, dried for approximately one hour at room temperature and dried in the drying closet at about 99° C. for approximately 16 hours.

Figure 2:
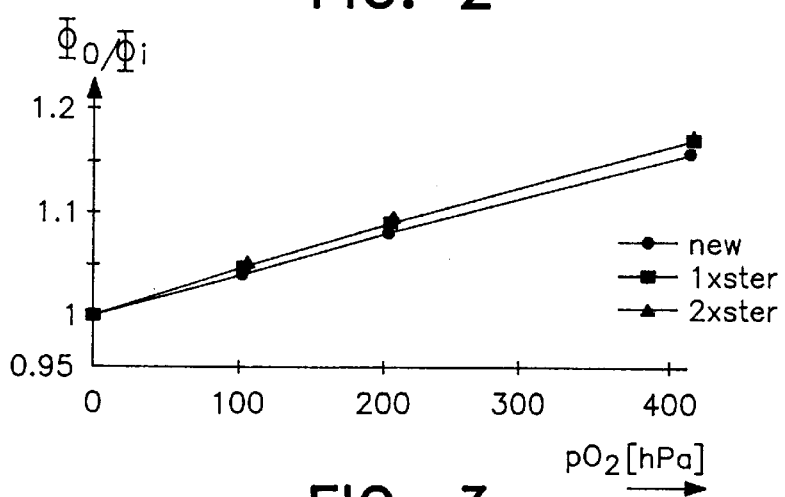

FIG. 2 depicts the calibration functions of a polyether imide membrane with tris(4,7-diphenyl-1,10-phenanthroline) ruthenium(II) perchlorate before and after hot vapor sterilization, whereby the partial pressure of oxygen is again plotted on the abscissa and the standardized phase shift of the luminescent membrane is plotted on the ordinate.

The pretreated, i.e., once sterilized membrane compared to the same membrane treated a second time in the autoclave, yields the numerical values indicated in the following Table.

| Vol.-% O₂ in measuring gas | Deviation in vol.-% O₂ |
|---|---|
| 0 | 0.06 |
| 10.3 | −0.12 |
| 20.55 | −0.38 |
| 41.96 | −0.85 |

EXAMPLE 3

Production of an optochemical sensor, calibration and purification with soda lye at an elevated temperature 0.31 g polysulfone by Aldrich are mixed with 2.81 g chlorofom and the polymer is dissolved in the solvent by agitation at room temperature. 1.25 g of the polymer solution are removed and agitated at room temperature with 0.0017 g tris(4,7-diphenyl-1,10-phenanthroline) ruthenium (II) perchlorate. The solution is applied on 175 μm substrate films by means of a doctor blade as a thin coat having a wet film thickness of 50 μm. After drying for about an hour at room temperature, the thus produced films are left in the drying closet at about 138° C. for about 16 hours. Up to the time of measuring, the membrane was stored in the dark at room temperature. For the purpose of calibration, the phase shift of the luminescent membrane was measured as a function of the oxygen partial pressure. After this, the membrane was exposed to 1N NaOH at 50° C. for 30 minutes, then rinsed with distilled water, allowed to dry in the dark for about 15 hours at room temperature and subsequently subjected to a new determination of the calibration function.

The Table below indicates the results of the membrane treated with NaOH, the measuring values of the treated membrane being based on the calibration function of the untreated membrane. The deviations before and after the NaOH treatment are expressed in vol.-% oxygen.

| Oxygen content in calibration gas [hPa] | Deviation of the membrane treated with 1N NaOH at 50° C. for 30 minutes from the untreated membrane, expressed in vol.-% O₂ deviation |
|---|---|
| 0 | 0.04 |
| 5.1 | 0.02 |
| 10.3 | −0.01 |
| 20.55 | −0.07 |
| 41.96 | −0.21 |
| 100 | −0.44 |

EXAMPLE 4

Production of an optochemical sensor, calibration and purification with diluted phosphoric acid at an elevated temperature
(Same batch as in Example 3)

0.31 g polysulfone by Aldrich are mixed with 2.81 g chlorofom and the polymer is dissolved in the solvent by agitation at room temperature. 1.25 g of the polymer solution are removed and agitated at room temperature with 0.0017 g tris(4,7-diphenyl-1,10-phenanthroline) ruthenium (II) perchlorate. The solution is applied on 175 μm substrate films by means of a doctor blade as a thin coat having a wet film thickness of 50 μm. After drying for about an hour at room temperature, the thus produced films are left in the drying closet at about 138° C. for about 16 hours. Up to the time of measuring, the membrane was stored in the dark at room temperature.

For the purpose of calibration, the phase shift of the luminescent membrane was measured as a function of the oxygen partial pressure. After this, the membrane was exposed to 2.5% phosphoric acid at 50° C. for 30 minutes, then rinsed with distilled water, allowed to dry in the dark for about 15 hours at room temperature and subsequently subjected to a new determination of the calibration function.

The Table below indicates the results of the membrane treated with phosphoric acid, the measuring values of the treated membrane being based on the calibration function of the untreated membrane. The deviations before and after the NaOH treatment with phosphoric acid are expressed in vol.-% oxygen.

| Oxygen content in calibration gas [hPa] | Deviation of the membrane treated with 2.5% H₃PO₄ at 50° C. for 30 minutes from the untreated membrane, expressed in vol.-% O₂ deviation |
|---|---|
| 0 | −0.02 |
| 5.1 | −0.04 |
| 10.3 | −0.06 |
| 20.55 | −0.13 |
| 41.96 | −0.25 |
| 100 | −0.53 |

EXAMPLE 5

Production of an optochemical sensor, calibration and sterilization 0.205 g PSU by Aldrich are mixed with 1.8435 g chloroform and the polymer is dissolved by agitation at room temperature. 1.32 g are removed from this solution and mixed with 1.24 mg Pt octaethylporphyrine ketone and stirred at room temperature until the dye has been completely dissolved. After this, sensitive layers having wet film thicknesses of 50 μm are applied on Mylar polyester membranes. These membranes are dried in the drying closet at 130° C. for about 15 hours.

Figure 3:
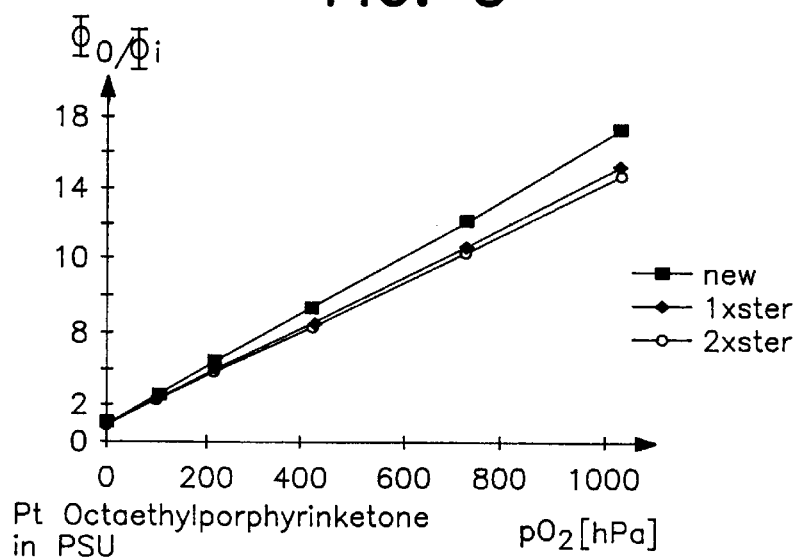

Characteristic curves are traced by means of intensity measurements: a characteristic curve of the unsterilized membrane, a characteristic curve of the once sterilized (60 min at 135° C.) membrane, and a characteristic curve of the twice sterilized membrane. (FIG. 3)

The Table below shows the deviations of the twice sterilized membrane from the once sterilized membrane, the first sterilization being regarded as a pretreatment.

| Oxygen content in calibration gas [hPa] | Deviation [vol.-% $O_2$] of the twice sterilized membrane from the once sterilized membrane dried at 130° C. |
|---|---|
| 0 | 0 |
| 10 | −0.31 |
| 21 | −0.72 |
| 40 | −1.46 |
| 100 | −4.25 |

What is claimed is:

1. An optochemical sensor comprising a luminescent dye incorporated in a polymer matrix, the luminescent dye having an emission capacity which is variable upon excitation with electromagnetic radiation by a detectable substance; the polymer matrix being formed, without plasticizer addition, of at least one polymer having a main chain containing phenyl groups, the polymer having a glass transition temperature of above 140° C. and comprising at least one member selected from the group consisting of a polysulfone, a polyether sulfone, a polyether imide and a polyoxyphenylene.

2. An optochemical sensor according to claim 1 wherein the electromagnetic radiation is light.

3. An optochemical sensor according to claim 1 wherein the detectable substance is a member selected from the group consisting of gaseous or dissolved oxygen, gaseous or dissolved $SO_2$, gaseous or dissolved $H_2O_2$, gaseous or dissolved chlorine, a nitrogen oxide and a halogenated hydrocarbon.

4. An optochemical sensor according to claim 1, wherein the luminescent dye comprises from 0.01 to 100 mMol dye per kg of polymer.

5. An optochemical sensor according to claim 4 wherein the luminescent dye comprises from 0.1 to 20 mMol dye per kg of polymer.

6. An optochemical sensor according to claim 1, wherein the luminescent dye is stable up to a temperature of at least 150° C. and is a member selected from the group consisting of an inorganic salt of a transition metal complex having an α-diimine ligand, an inorganic salt of terpyridine, a transition metal complex of a porphyrine or of a porphyrine derivative, a polycyclic aromatic hydrocarbon and campherchinone.

7. An optochemical sensor according to claim 6 wherein the inorganic salt of a transition metal complex having an α-diimine ligand is a member selected from the group consisting of a tris(4,7-diphenyl-1,10-phenanthroline) ruthenium(II) salt, a tris(1,10-phenanthroline) ruthenium (II) salt and a tris-2,2'-bipyridyl ruthenium(II) salt; the inorganic salt of terpyridine is osmium terpyridine; the transition metal complex of a porphyrine or of a porphyrine derivative is a member selected from the group consisting of a complex of the tetraphenylporphyrine of Pt, a complex of the tetraphenylporphyrine of Pd, a complex of the octaethylporphyrine ketone of Pt, a complex of the octaethylporphyrine ketone of Pd, a complex of the tetrapentafluorophenylporphyrine of Pt, a complex of the tetrapentafluorophenylporphyrine of Pd, a complex of the octaethylporphyrine of Pt, and a complex of the octaethylporphyrine of Pd; and the polycyclic aromatic hydrocarbon is a member selected from the group consisting of decacyclene, pyrene and a pyrene derivative.

8. An optochemical sensor according to claim 1 in combination with and on a substrate.

9. An optochemical sensor according to claim 8, wherein the substrate is an optically inactive light-permeable polymer that is insoluble in and resistant to a member selected from the group consisting of an organic solvent, an acid, a base and water.

10. An optochemical sensor according to claim 8 wherein the substrate is a member selected from the group consisting of polyester, polymethylmethacrylate and glass.

11. An optochemical sensor according to claim 10 wherein the polyester is PET.

12. An optochemical sensor according to claim 1 in combination with and covered by an optically insulating or protecting layer permeable to a substance to be analyzed.

13. An optochemical sensor according to claim 12, wherein the optically insulating layer comprises a member selected from the group consisting of coarsely porous polytetrafluoroethylene, a copolymer of 2,2-bis-trifluoromethyl-4,5-difluoro-1,3-dioxolene and tetrafluoroethylene, and silicone.

* * * * *